(12) United States Patent
Colmenares Mora et al.

(10) Patent No.: US 12,022,822 B2
(45) Date of Patent: Jul. 2, 2024

(54) ANTIBACTERIAL MEDICAL PRODUCT AND METHOD FOR PRODUCING SAME

(71) Applicant: Oerlikon Surface Solutions AG, Pfaffikon, Pfaffikon SZ (CH)

(72) Inventors: Carmen Leonor Colmenares Mora, Malans (CH); Arnd Mueller, Malans (CH); Albert Peter Gerhard Janssen, Chur (CH)

(73) Assignee: OERLIKON SURFACE SOLUTIONS AG, PFÄFFIKON, Pfäffikon Sz (CH)

( * ) Notice: Subject to any disclaimer, the term of this patent is extended or adjusted under 35 U.S.C. 154(b) by 160 days.

(21) Appl. No.: 17/179,795

(22) Filed: Feb. 19, 2021

(65) Prior Publication Data
US 2021/0169071 A1 Jun. 10, 2021

Related U.S. Application Data

(63) Continuation of application No. 16/184,067, filed on Nov. 8, 2018, now Pat. No. 10,945,430, which is a
(Continued)

(51) Int. Cl.
*A61L 27/52* (2006.01)
*A01N 25/08* (2006.01)
(Continued)

(52) U.S. Cl.
CPC ............. *A01N 25/08* (2013.01); *A01N 59/16* (2013.01); *A61L 27/28* (2013.01); *A61L 27/54* (2013.01);
(Continued)

(58) Field of Classification Search
CPC .................................. A61L 27/52; A61L 27/28
See application file for complete search history.

(56) References Cited

U.S. PATENT DOCUMENTS

| 5,685,961 A | 11/1997 | Pourrezaei et al. |
| 6,261,322 B1 | 7/2001 | Despres, III et al. |

(Continued)

FOREIGN PATENT DOCUMENTS

| CN | 1304627 C | * | 3/2007 |
| CN | 1304627 C | | 3/2007 |

(Continued)

OTHER PUBLICATIONS

Yuan et al. Protection Properties of TiN Coating Prepated by Arc Ion Plating Magnetron Sputtering on TC11 Titanium Alloy. Proceedings of Sino-Swedish Structural Materials Symposium, 2007 pp. 142-146 (Year: 2007).*

(Continued)

*Primary Examiner* — Cachet I Proctor
(74) *Attorney, Agent, or Firm* — Pearne & Gordon LLP

(57) ABSTRACT

A medical product including an antibacterial hard material coating, which is applied to a main body and which includes biocide. The hard material coating includes at least one inner layer and one outer layer, wherein the biocide concentration in the outer layer is substantially constant and greater than the biocide concentration in the inner layer and the biocide concentration in the inner layer is greater than or equal to 0.2 at %.

9 Claims, 4 Drawing Sheets

Related U.S. Application Data continuation of application No. 13/809,644, filed as application No. PCT/EP2011/002405 on May 16, 2011, now Pat. No. 10,143,196.

(60) Provisional application No. 61/362,888, filed on Jul. 9, 2010.

(51) Int. Cl.

| | | |
|---|---|---|
| *A01N 59/16* | (2006.01) | |
| *A61L 27/28* | (2006.01) | |
| *A61L 27/54* | (2006.01) | |
| *A61L 29/08* | (2006.01) | |
| *A61L 29/16* | (2006.01) | |
| *A61L 31/08* | (2006.01) | |
| *A61L 31/16* | (2006.01) | |

(52) U.S. Cl.
CPC ............... *A61L 29/08* (2013.01); *A61L 29/16* (2013.01); *A61L 31/08* (2013.01); *A61L 31/16* (2013.01); *A61L 2300/104* (2013.01); *A61L 2300/404* (2013.01); *A61L 2300/608* (2013.01)

(56) References Cited

U.S. PATENT DOCUMENTS

| | | |
|---|---|---|
| 6,333,093 B1 | 12/2001 | Burrell et al. |
| 8,029,917 B2 | 10/2011 | Spain et al. |
| 8,353,949 B2 | 1/2013 | Weber et al. |
| 9,011,965 B2 | 4/2015 | Gan et al. |
| 2002/0042656 A1 | 4/2002 | Hunter et al. |
| 2004/0117007 A1 | 6/2004 | Whitbourne et al. |
| 2006/0198903 A1 | 7/2006 | Storey et al. |
| 2008/0147177 A1 | 6/2008 | Scheuermann et al. |
| 2010/0211158 A1 | 8/2010 | Haverty et al. |
| 2011/0104477 A1 | 5/2011 | Wagener et al. |
| 2012/0094143 A1 | 4/2012 | Zhang et al. |
| 2013/0108879 A1 | 5/2013 | Mochizuki et al. |
| 2013/0302512 A1 | 11/2013 | McEntire et al. |
| 2014/0308628 A1 | 10/2014 | Carradò et al. |

FOREIGN PATENT DOCUMENTS

| | | |
|---|---|---|
| DE | 10 2005 044 361 A1 | 3/2007 |
| DE | 10 2008 001 014 A1 | 10/2009 |
| WO | 02/17984 A1 | 3/2002 |
| WO | 2005/065603 A1 | 7/2005 |
| WO | 2007/028645 A2 | 3/2007 |

OTHER PUBLICATIONS

International Search Report for PCT/EP2011/002405 dated Oct. 27, 2011.

Kelly, P.J., et al., "A study of the antimicrobial and tribological properties of TiN/Ag nanocomposite coatings" Surface & Coatings Technology, 2009, v.204, 1137-1140.

Ewald, Andrea, et al., "Antimicrobial titanium/silver PVD coatings on titanium" BioMedical Engineering Online, 2006, 5:22, 1-10.

Xiao, Shiqin, et al., "Comparison of TiN deposition by rf magnetron sputtering and electron beam sustained arc ion plating" Thin Solid Films, 334 (1998) pp. 173-177.

Yuan, Jian-Peng, et al., "Protection Properties of TiN Coating Prepared by Arc Ion Plating and Magnetron Sputtering on TC11 Titanium Alloy" Proceedings of Sino-Swedish Structural Materials Symposium, 2007, pp. 142-146.

\* cited by examiner

ANTIBACTERIAL MEDICAL PRODUCT AND METHOD FOR PRODUCING SAME

This is a continuation of U.S. application Ser. No. 16/184,067 filed Nov. 8, 2018 which was a continuation of U.S. application Ser. No. 13/809,644 filed on May 17, 2013, which is the national stage of PCT Application No. PCT/EP2011/002405 filed on May 16, 2011, which claims benefit of U.S. Application No. 61/362,888 filed on Jul. 9, 2010. The contents of these applications are incorporated herein by reference in their entireties.

The present invention relates to a medical product, in particular a tool or instrument comprising an antibacterial hard material coating applied to a main body.

DEFINITIONS AND MEASURING METHODS

In accordance with council directive 93/42/EEC of 14 Jun. 1993 concerning medical devices, 'medical device' means any instrument, apparatus, appliance, software, material or other article, whether used alone or in combination, including the software intended by its manufacturer to be used specifically for diagnostic and/or therapeutic purposes and necessary for its proper application, intended by the manufacturer to be used for human beings for the purpose of:

- diagnosis, prevention, monitoring, treatment or alleviation of disease;
- diagnosis, monitoring, treatment, alleviation of or compensation for an injury or handicap;
- investigation, replacement or modification of the anatomy or of a physiological process;
- control of conception;

and which does not achieve its principal intended action in or on the human body by pharmacological, immunological or metabolic means, but which may be assisted in its function by such means.

Furthermore, in accordance with council directive 93/42/EEC of 14 Jun. 1993 concerning medical devices, 'accessory' means an article which whilst not being a device is intended specifically by its manufacturer to be used together with a device to enable it to be used in accordance with the use of the device intended by the manufacturer of the device.

For the purpose of this patent, a 'medical product comprises both a medical device as well as an accessory according to the definitions of medical device and accessory according to council directive 93/42/EEC of 14 Jun. 1993 concerning medical devices, but also for veterinary applications, yet with the exception of:

- endoprostheses resp. medical devices that are implanted in the body and are intended to remain there permanently or at least for a longer period of time;
- substances and further medical devices or accessories of a medical device that have no firm surface.

Hard materials have a great hardness and high wear resistance. These substances are of great technical importance. Due to their manifold properties and different fields of application it is difficult to find a comprehensive definition for hard materials. The following characteristic properties apply to most hard materials: high degree of hardness, high wear resistance, high melting points, chemical stability, further mechanical properties such as e.g. tensile strength, strain or flexural strength, depend strongly on the type of hard material. This is also valid for electrical conductivity. The properties of hard materials generally correlate closely with the electronic structure of these compounds. Depending on whether metallic or covalent compounds are present, clear differences between metallic and non-metallic hard materials will emerge.

In the context of the present invention, designating a coating as hard material coating takes into account in particular the layer hardness or the hardness of the layer system and a characteristic hardness of at least 1500 HV (hardness according to Vickers) or 17 GPa (Martens hardness).

Reported hardness values were measured according to the Martens hardness testing process using a "Fischerscope H100C". A Vickers diamond was used as indenter. The Martens hardness testing method is standardized in DIN EN ISO 14577 (metallic materials—instrumented indentation test for hardness and materials parameters). According to this method, during the loading and unloading phase, the force and indentation depth are continuously measured. The Martens hardness is defined as the ratio of the maximum force to the respective contact surface and its value is given using the unit Newton per square millimeter. The Martens hardness HM is calculated on the basis of the measurement values of the force/indentation depth curve when the applied test force is increased, preferably after a determined test force has been reached, and in this case, when using a Vickers diamond as indenter, the following definition is true:

$$HM[Nmm^{-2}] = \frac{F}{A_s(h)} = \frac{F}{26.44 \cdot h^2}$$

where F is the force [N] and h is the indentation depth under test force [mm].

The hardness definition given can in principle be applied also to thin layers. However, some peculiarities must be taken into account. During penetration of the indenter, a deformation of layer and substrate will usually occur simultaneously. A compound hardness $H_c$ is thus determined, for which the following relation applies:

$$H_c = \frac{V_f}{V_f + V_s} \cdot H_f + \frac{V_s}{V_f + V_s} \cdot H_s$$

where $H_f$, $H_s$ are the layer resp. substrate hardness and $V_f$, $V_s$ are the deformed layer resp. substrate volume The deformed substrate volume decreases as the indentation depth of the indenter decreases and thus, the smaller the indentation depth and thus the test force, the closer the determined compound hardness is to the effective layer hardness. When measuring the hardness of layer systems, for indentation depths $$h \leq \frac{1}{10} df \ldots \frac{1}{7} df$$

where df is the layer thickness it can generally be assumed (according to the Bückle's rule) that the determined hardness is approximately the same as the layer hardness. In the frame of the present invention, the reported layer hardness values were determined taking into account the Bückle's rule.

The class of adhesiveness was determined according to the Rockwell test. When testing the layer bonding by means of the Rockwell test according to the guidelines 3198

"Coating (CVD, PVD) of cold forging tools" and 3824-4 "Quality assurance of PVD and CVD hard coating—Inspection planning of hard coatings" of the VDI (Association of German Engineers), the size and type of the network of cracks as well as the spalling of the coating in the edge area of an HRC (Rockwell value) indentation are assessed and this allows direct conclusions to be made regarding the adhesive strength according to the schema shown in FIG. 1 resp. series of images for determining the class of adhesiveness of PVD layers on tools or high-speed steel (HF1: very good to HF6: very poor). In order to use this method, the Rockwell hardness of the base material and the layer thickness or thickness of the layer system must not be smaller than 54 HRC respectively not larger than 5 μm. The evaluation is carried out directly on the microscope by means of the HRC indentation (150 kp) magnified a hundred times.

A 3-range colorimeter MIKRO COLOR II from the company Dr. Lange, which generates diffuse reflections on the sample surface by means of a xenon flash lamp and then measures them according to the norm DIN 5033, was used as a measuring device for measuring the color of the surface of the layer systems. As reference standard for the calibration, a white standard with standard color values X: 84.6, Y: 89.4 and Z: 91.8 was used. After each color measurement, the color values resulting therefrom were displayed in the display of the colorimeter according to the CIELAB three-dimensional coordinate system (L*a*b), where the a* axis describes the green or red ratio of a color with values from −150 to 100 (negative values for green and positive values for red), the b* axis describes the blue or yellow ratio of a color with values from −100 to 150 (negative values for blue and positive values for yellow) and the L* axis describes the brightness (luminance) of the color with values from 0 to 100.

BACKGROUND

Nowadays, different products are available on the market which claim to have antibacterial or antimicrobial properties. Attempts are made to provide hygiene and medical products with antibacterial resp. antimicrobial properties, in particular in order to prevent infectious diseases. It is known to use silver and its ions as non-organic biocide for treating materials, which then in the course of time release the biocide they contain, so that the colonization or proliferation of microorganisms on these materials and even in their vicinity is reduced or completely prevented. For this purpose, several antimicrobial silver technologies have been researched and developed to date. Other known non-organic biocides are for example also copper and zinc, which for certain reasons such as for example higher toxicity and less efficient biocide efficacy by comparison with silver, are less in demand for medical technology applications.

The HyProtect™ technology for example allows thin (<200 nm) antimicrobial coatings to be applied on, among others, medical products, said coatings consisting of a combination layer of pure silver deposited by means of a PVD (physical vapor deposition) process and of a silicon oxide layer deposited by means of a CVD (chemical vapor deposition) process. This technology makes it possible to generate especially desired optical and antimicrobial properties on different surfaces, but does not allow a true improvement of the anti-wear protection.

It is also known to use physical and/or chemical and/or plasma assisted chemical coating methods under vacuum, i.e. PVD and/or CVD and/or PACVD (plasma assisted CVD) coating of medical products with hard material layers (such as for example with TiN, CrN and DLC). This generally allows desired optical as well as tribological properties to be achieved on the surface of a medical product. However, these do not exhibit sufficient antimicrobial efficacy.

The applicant has in their product portfolio various coatings that have been developed especially for medical products, in order to impart onto the surface of these medical products specific tribological properties as well as defined optical properties. In addition to an increased wear-resistance and improved friction properties, these coatings achieve in particular defined shining or matt colors.

Examples of layer systems and colors are:
TiN→gold
AlTiN or an a-C:H→black
TiAlN→bronze
CrN→silver
WC/C→grey.

Examples of layer systems and tribological and/or desired optical properties for medical devices are:
TiN→for safely marking implant stem provisionals
TiN and WC/C→for wear resistance and reduction of friction of drill guide elements
WC/C and CrN→for wear resistance of dental drills
WC/C→for reduction of friction and/or for anti-wear protection of bone fastening tools, tooth implant fastening tools, bone drills, bone saws, implantation guns, artery cleaning springs
WC/C→for transmission of anti-reflective properties onto eye surgery blades
DLC→for anti-corrosion protection and/or for safely marking dental calculus removers and/or also for transmission of anti-reflective properties (DLC is also called a-C:H)

Several research projects on PVD and/or CVD and/or PACVD deposition of antimicrobial Ag-containing hard layers (such as for example Ag—TiN, Ag—CrN and Ag-a-C:H) for medical purposes, in particular for coating endoprostheses, have also already been published by different research institutions. In these research projects, it was attempted to research antimicrobial and/or tribological properties as well as in some cases also biocompatibility of the thus formed layer systems, however without taking any account of the optical properties such as color and reflection, which play a very important role for some medical-technical tools and instruments.

Own development projects have shown that silver doping of hard layers, using the example of titanium nitride, can negatively affect critical layer parameters such as adhesive strength, hardness and roughness (see FIGS. 1, 2, 3). It has in particular been observed that the higher the silver content was, the lower the adhesive strength onto the main body. Furthermore, by doping with silver, the optical properties of the initial layer system could be influenced (see FIG. 4).

BRIEF SUMMARY

The aim of the present invention is to improve the disadvantages above described of the state of the art. In particular, a suitable coating for medical products should be provided that yields predetermined antibacterial properties and provides an improvement of the tribological properties already exhibited by the substrate such as for example wear resistance and reduction of the friction. For this, the coating must be mainly able to exhibit sufficient adhesiveness to the main body of the medical product. The corrosion resistance should remain intact or at least decrease only within admissible limits. In doing so, the attempt is preferably made to give the medical products those optical properties that lead to acceptance by the user.

It is in particular an aim of the present invention to achieve such properties on surfaces of said medical products, in particular of tools and instruments, by means of coatings, in particular by means of PVD and/or PACVD coatings.

Furthermore, it is necessary to take into account the fact that the substrate temperature during the coating process should be commensurate to the heat resistance of the substrate material, i.e. the maximum admissible temperature with respect to the substrate material should not be exceeded.

In particular, a temperature of 300° C. should as a rule not be exceeded for the coating of medical products such as for example corresponding instruments and tools due to the commonly used types of substrate, such as for example stainless steel 1.4542.

The aim is achieved according to the invention by means of an antibacterial hard material coating, which is applied to a main body (1) and which comprises biocide. The hard material coating includes at least one inner layer (5) with a thickness d1 of at least 0.2 μm and one outer layer (9) with a thickness d2 of at least 0.5 μm. The inner layer (5) is arranged between the outer layer and the main body (1) and the outer layer (9) contains a biocide concentration bcI greater than or equal to 2 at % and that is substantially constant throughout the entire layer thickness. Indications relating to the biocide concentration in the context of this description always refer to an average over at least 20 nm depth. The inner layer (5) has a biocide concentration with a maximum value bcII greater than or equal to 0.2 at %. The biocide concentration of the inner layer (5) over its entire layer thickness is smaller than the substantially constant biocide concentration bcI of the outer layer (9). The silver concentration in the inner layer (5) along its layer thickness can vary and increase especially in the direction from the main body (1) to the outer layer (9). The layer system designed according to the invention thus exhibits an improved adhesiveness to the substrate as compared with a layer system without the inventive inner layer.

BRIEF DESCRIPTION OF THE DRAWINGS

The invention will hereinafter be explained in more detail on the basis of examples, with reference to the figures shown. The figures show:

FIG. 5: design by way of example of a coating resp. of a layer system for the inventive production of antibacterial medical products, with:

(1) main body
(2) mechanical and/or electrochemical preprocessing to increase the adhesive strength
(3) bonding layer and/or anti-wear protection layer
(5) inventive inner layer comprising biocide
(7) intermediate layer comprising biocide with a higher biocide concentration than that of the outer layer
(9) outer layer
(10) mechanical post-processing such as e.g. polishing for reducing the roughness

DETAILED DESCRIPTION

Different PVD coating methods were used for the production of silver doped TiN layers.

Figure 1A:
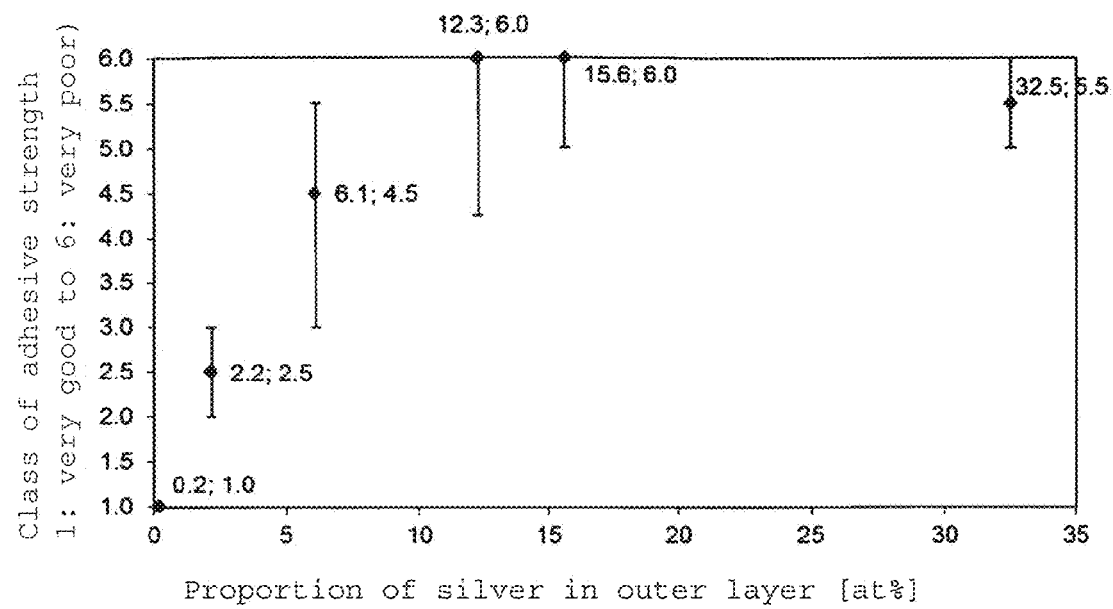
FIG. 1*a*: behavior: adhesive strength vs. concentration of silver of Ag/TiN layer systems without inventive integrated inner layer deposited on polished (Ra: 0.05 μm) alloyed cold work steel 1.2842.
Figure 1B:
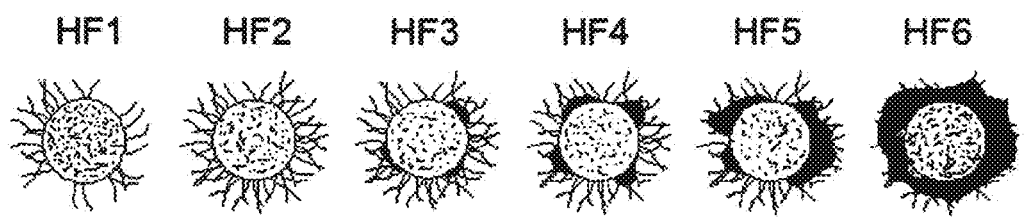
FIG. 1*b*: diagrammatic representation of the classes of adhesive strength
Figure 6:
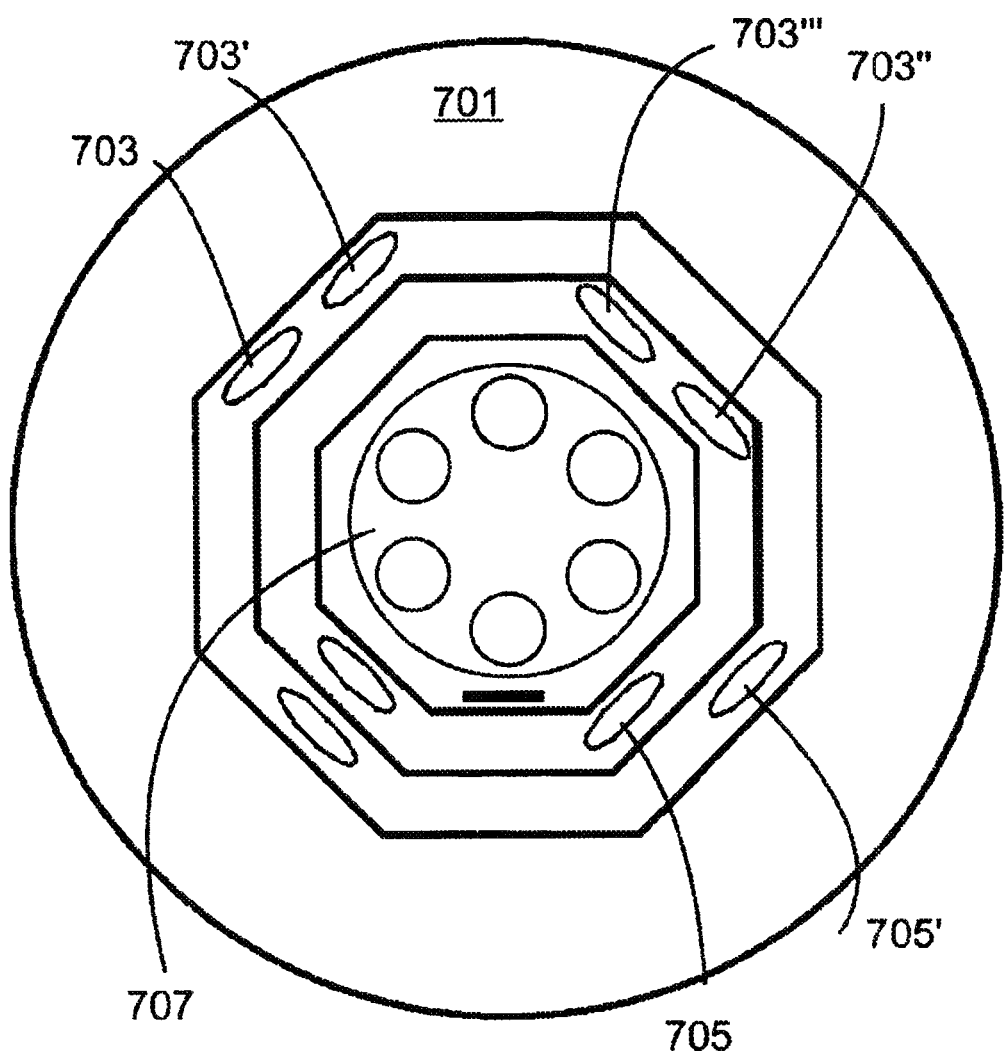
FIG. 6: arrangement by way of example of a coating facility for the inventive production of antibacterial medical products.

Example 1: By means of a combined arc/sputter process resp. of a hybrid AIP+MSIP process, silver doped TiN layer systems resp. Ag/TiN layer systems were produced. FIG. 6 illustrates diagrammatically an arrangement of a vacuum coating facility 701, wherein the layer systems with biocide effect were deposited onto the main body of medical products and/or test bodies. Separate titanium targets 703, 703', 703'', 703''' and silver targets 705, 705' were used as material source. Layer systems with different silver concentrations were produced by varying the arc current at the Ti targets 703, 703', 703'', 703''', the sputter performance at the Ag targets 705, 705' and the bias voltage at the substrate. It would furthermore be possible to vary the silver concentration by varying the number of the active titanium and/or silver targets. The Ag/TiN layers were deposited under controlled pressure in $Ar/N_2$ atmosphere at a process pressure of 0.02 mbar. The substrates were placed during the coating in a carrousel arrangement 707 with double and triple rotation. The speed of rotation of the substrates was maintained constant. After corresponding heating and etching processes in the vacuum coating chamber, a very thin bonding layer of TiN (thickness ≤0.3 μm) was deposited by means of the AIP technique onto the surface of the test bodies or medical products of different steel grades and also of hard metal and then the Ag/TiN layer was deposited by means of a combination of AIP and MSIP techniques with constant process parameters, as described above. FIGS. 1 to 4 illustrate the influence of the silver concentration on the hardness, roughness and optical properties that were deposited with different Ag sputter performances and otherwise identical process parameters. It could be established (as represented in FIG. 1*a*) that at increased silver concentrations, the adhesiveness deteriorates considerably.

Figure 5:
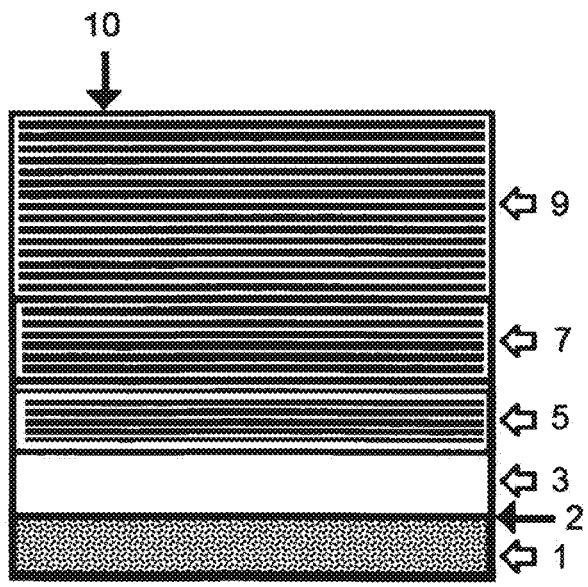

The inventors have observed that by including an inner layer 5 between the main body 1 and the outer layer 9 provided with an increased concentration of silver, as represented in FIG. 5, the adhesive strength of Ag/Ti layer systems with increased silver content can be significantly improved.

This also applies when an intermediate layer 7 is provided between the inner layer 5 and the outer layer 9 and which has an increased concentration as compared with the outer layer 9 and can serve as a reservoir of silver for the outer layer 9.

Additionally, a bonding layer 3 or anti-wear protection layer 3 can be provided between the main body 1 and the inner layer 5, which increases the adhesiveness even more.

As the above example shows, it was possible by means of the inventive sequence of layers and of the method to clearly improve the adhesive strength of the layers with increased silver content. A further possibility according to the following example 2 consists in integrating the biocide in DLC layers. Starting from the substrate, for example a bonding layer, for example chromium, is applied. Subsequently a DLC layer is deposited by means of PACVD and simultaneously the silver target is activated. Here too, only little silver is first incorporated for example by means of a low sputter performance. The concentration is then increased, for example by increasing the sputter power whilst the coating parameters otherwise remain the same. At the end, the silver concentration is kept constantly high during the coating, in order to produce the outer layer with constant biocide concentration. Again, an inventive layer was generated with improved adhesive properties as compared with the state of the art.

Figure 2:
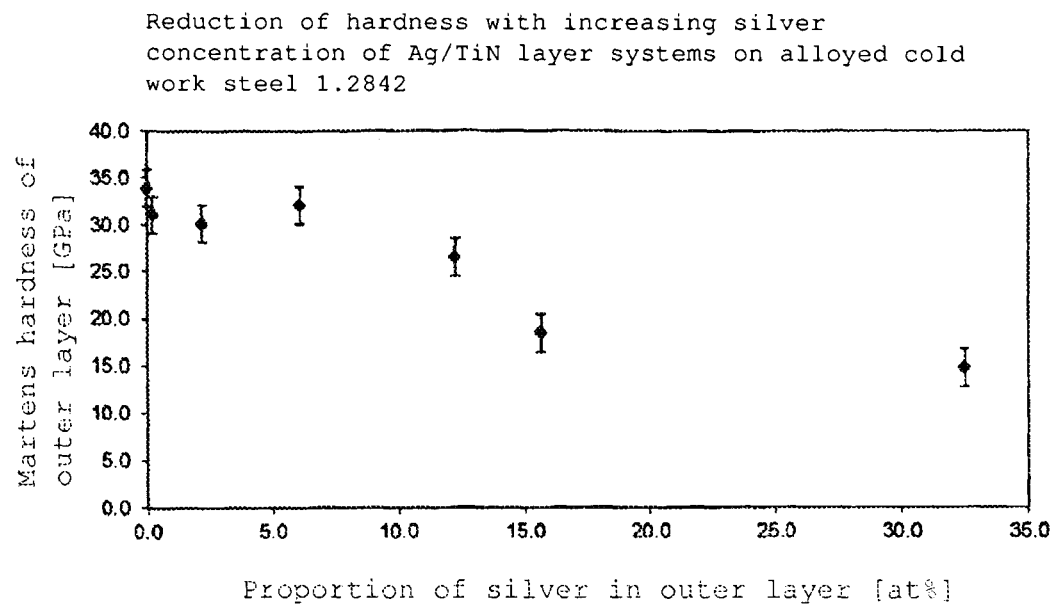
FIG. 2: behavior: Martens hardness vs. concentration of silver of Ag/TiN layer systems deposited on polished (Ra: 0.05 μm) alloyed cold work steel 1.2842
Figure 4:
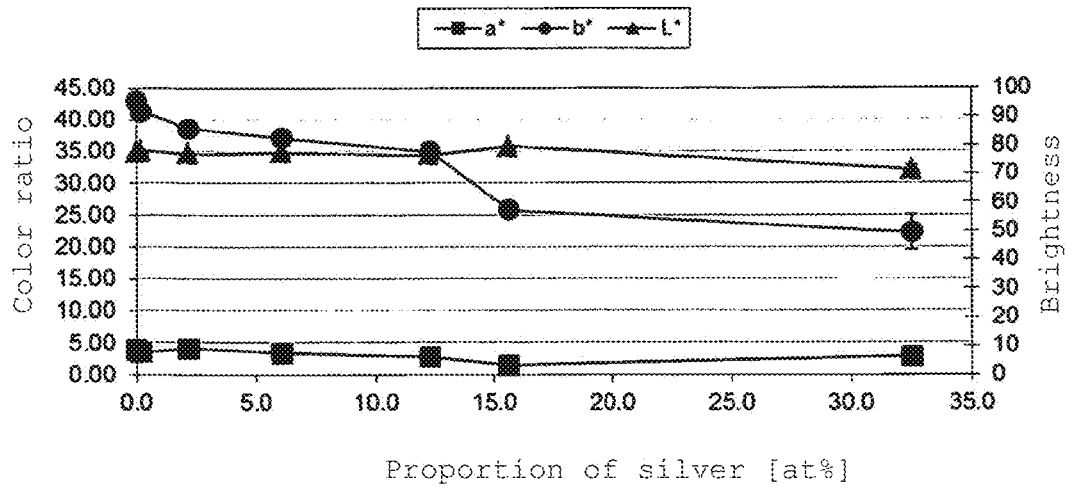
FIG. 4: behavior: optical properties using the example of color values according to the CIELAB system vs. concentration of silver of Ag/TiN layer systems deposited on polished (Ra: 0.05 μm) alloyed cold work steel 1.2842

The question then arises as to how the concentration value of the biocide can be limited. One would actually expect that the higher the biocide concentration is, the better the effect would be. However, surprisingly, the measurements performed by the inventors contradict this. Additionally, from a concentration greater than 15 at %, the hardness of the layer, as represented in FIG. 2, decreases drastically and, as illustrated in FIG. 4, the color appearance varies greatly. It is thus proposed to use biocide concentrations of up to 15 at %, preferably of up to 13 at %.

Figure 3:
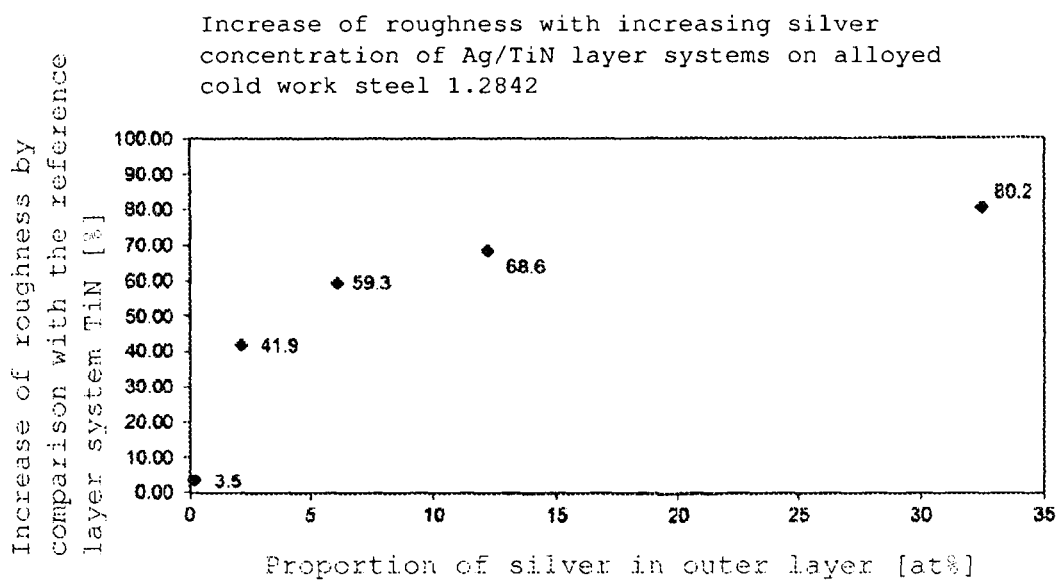
FIG. 3: behavior: roughness vs. concentration of silver of Ag/TiN layer systems deposited on polished (Ra: 0.05 μm) alloyed cold work steel 1.2842

It can happen that when incorporating silver, the surface of the coated product, in particular medical product, will exhibit increased roughness, as represented for example in FIG. 3. The inventors have observed that increased roughness leads to a reduction of the biocide effect. This can be prevented in that the surface is subjected to a post-processing, in particular a mechanical post-processing such as polishing, wet blasting or lapping or a suitable chemical polishing. Due to the constancy of the biocide concentration in the outer layer, this post-processing will essentially no affect the biocide effect when the medical product is used.

The invention claimed is:

1. A medical product with an antibacterial hard material coating comprising a biocide applied to a main body, the hard material coating consisting of a bonding layer, an inner layer, and an outer layer, wherein the inner layer is between the outer layer and the main body, the bonding layer is between the inner layer and the main body, the bonding layer contains essentially no biocide, the outer layer has a biocide concentration (bcI) of 2 at % to 15 at %, the inner layer has a biocide concentration (bcII) that is greater than or equal to 0.2 at % and less than bcI, and the biocide concentration (bcII) of the inner layer increases in a direction from the main body toward the outer layer.

2. The medical product of claim 1, wherein the inner layer has a thickness (d1) of at least 0.2 µm.

3. The medical product of claim 1, wherein the outer layer has a thickness (d2) of at least 0.5 µm.

4. The medical product of claim 1, wherein bcI is substantially constant throughout the outer layer.

5. The medical product of claim 1, the hard material coating comprising one or more of TiN, TiAlN, AlTiN, CrN, WC/C or a-C:H.

6. The medical product of claim 1, wherein the biocide is a non-organic biocide.

7. The medical product of claim 6, wherein the non-organic biocide is silver.

8. The medical product of claim 1, wherein the outer layer has a hardness of 17 to 32 GPa.

9. The medical product of claim 1, wherein the inner layer is diamond-like carbon (DLC).

* * * * *